(12) United States Patent
Goldsmith

(10) Patent No.: US 7,871,636 B2
(45) Date of Patent: Jan. 18, 2011

(54) AQUEOUS, FLOWABLE CONCENTRATE COMPOSITION OF PENDIMETHALIN

(75) Inventor: Andrew Goldsmith, Waterlooville (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/553,153

(22) PCT Filed: Apr. 13, 2004

(86) PCT No.: PCT/EP2004/003873

§ 371 (c)(1),
(2), (4) Date: Feb. 7, 2006

(87) PCT Pub. No.: WO2004/089088

PCT Pub. Date: Oct. 21, 2004

(65) Prior Publication Data

US 2006/0122066 A1     Jun. 8, 2006

(30) Foreign Application Priority Data

Apr. 14, 2003 (EP) ................... 03008556

(51) Int. Cl.
*A01N 25/34* (2006.01)
*A01N 33/18* (2006.01)

(52) U.S. Cl. ........................ 424/408; 504/347

(58) Field of Classification Search .............. 504/116.1; 424/457, 468
See application file for complete search history.

(56) References Cited

U.S. PATENT DOCUMENTS

| 4,874,425 A | 10/1989 | Kimpara et al. |
| 5,461,027 A | 10/1995 | Bergman |
| 5,705,174 A * | 1/1998 | Benoff et al. ............... 424/408 |
| 5,910,314 A | 6/1999 | Benoff et al. |
| 6,013,287 A | 1/2000 | Bunczek et al. |

FOREIGN PATENT DOCUMENTS

| EP | 0 445 603 A1 | 9/1991 |
| EP | 0 249 770 B1 | 8/1993 |
| EP | 0 747 116 B1 | 12/1996 |
| EP | 0 823 993 B1 | 2/1998 |
| EP | 279068 * | 8/1999 |
| EP | 0 711 506 B1 | 4/2003 |
| WO | WO 00/05951 A1 | 2/2000 |
| WO | WO-0005951 * | 2/2000 |
| WO | WO 02/15690 A1 | 2/2002 |

* cited by examiner

*Primary Examiner*—Alton N Pryor
(74) *Attorney, Agent, or Firm*—Rothwell, Figg, Ernst & Manbeck, P.C.

(57) ABSTRACT

The present invention relates to aqueous concentrate compositions of pendimethalin which are flowable, have improved storage stability and do not show a slowed release of active ingredient. The composition contains i. particles a) of microencapsulated pendimethalin, ii. particles b) of non-encapsulated pendimethalin and iii. at least one surface-active substance.

13 Claims, No Drawings

AQUEOUS, FLOWABLE CONCENTRATE COMPOSITION OF PENDIMETHALIN

CROSS REFERENCE TO RELATED APPLICATION

This application is a 35 USC §371 National Phase Entry Application from PCT/EP2004/003873, filed Apr. 13, 2004, and designating the United States.

The present invention relates to aqueous concentrate compositions of pendimethalin which are flowable and have improved storage stability.

Water-insoluble pesticides are often formulated into suspension concentrates which are also referred to as aqueous flowables. Suspension concentrates are aqueous compositions containing the pesticide as fine particles which are dispersed in the aqueous medium. The concentration of the pesticide in such concentrates is usually higher than 100 g/l and mostly at least 200 g/l. Suspension concentrates have the desirable characteristics of a liquid that may be poured or pumped and which can easily be diluted with water to the desired concentration required for application. In contrast to emulsion concentrates the suspension concentrates have the added advantage of not requiring the use of water-immiscible organic solvents.

Problems which are associated in general with suspension concentrates are settling and caking resulting in instability of the formulation, difficulty in processing and unreliability of usage. These problems are pronounced in case of low-melting pesticides, such as pendimethalin (common name for N-(1-ethyl propyl)-2,6-dinitro-3,4-dimethyl anilin). A further problem associated with formulations of pendimethalin results from the tendency of pendimethalin to form large crystals upon aging resulting in an increased settling of pendimethalin particles and thus in an instability, difficulty in processing and unreliability of usage. These problems become most serious when storing aqueous suspension concentrates of pendimethalin at temperatures above 35° C. and especially above 40° C.

U.S. Pat. No. 4,874,425 discloses an aqueous concentrate composition of pendimethalin which comprises sodium or calcium lignin sulfonate as stabilizer.

EP 249 770 discloses stable suspension concentrates of pendimethalin which are prepared by emulsifying molten pendimethalin in hot water, adding a surfactant and anti-foaming agents to provide a droplet size of the pendimethalin droplets of about 2 to 10 µm and cooling the hot emulsion to ambient temperature while agitating.

EP-A-445 603 teaches to stabilize aqueous suspension concentrates of water-insoluble pesticides by using a liquid polyoxyalkylene-polyoxypropylene-copolymer.

EP-A-823 993 teaches an aqueous microcapsule composition which contains pendimethalin being microencapsulated by a pH-sensitive polymeric material.

Although the suspension concentrates of pendimethalin are stable at ambient temperature, their storage stability is poor at higher temperatures, especially when the suspension concentrate is stored at temperatures exceeding 35° C. and most pronounced at temperatures exceeding 40° C.

It is known from U.S. Pat. No. 5,705,174 and U.S. Pat. No. 5,910,314 that aqueous concentrate composition of pendimethalin particles which are encapsulated by a polymeric wall material (microencapsulated pendimethalin) the tendency to form large crystals is reduced. These compositions have an improved storage stability. Unfortunately, microencapsulation of pendimethalin tends to slow the release of the active ingredient.

Therefore, it is an object of the present invention to provide an aqueous concentrate composition of pendimethalin which has an improved storage stability at higher temperatures and which does not show a slowed release of the active ingredient.

This object is solved by an aqueous concentrate composition of pendimethalin which contains both microencapsulated pendimethalin particles and particles of non-encapsulated pendimethalin and at least one surface-active substance.

The compositions of the invention are free flowable compositions, wherein both the microencapsulated pendimethalin particles and the non-encapsulated pendimethalin particles are finely dispersed in the aqueous suspension medium. These compositions remain stable for months at temperatures exceeding 35° C. and even at temperatures exceeding 45° C. Moreover, these compositions do not show a slowed release of active ingredient.

The compositions according to the invention usually contain pendimethalin at a total concentration of from 200 to 600 g/l, preferably of from 300 to 550 g/l and especially of from 350 to 450 g/l.

The compositions according to the invention in general contain microencapsulated pendimethalin particles and non-encapsulated pendimethalin particles in a weight ratio of from 1:9 to 9:1, preferably from 1:5 to 5:1, in particular from 1:4 to 4:1, especially of from 1:3 to 3:1, more preferably from 1:2 to 2:1 and most preferred of from 2:3 to 3:2.

According to the invention, one, part of the pendimethalin particles in the composition are microencapsulated pendimethalin particles. In microencapsulated pendimethalin the pendimethalin is encapsulated within a thin water-insoluble polymeric wall material. Examples for suitable wall materials are polyamide, polysulfonamide, polyester, polycarbonate, polyurethane or polyurea. Preferred wall materials are polyurethane and most preferred polyurea. The amount of polymeric wall material in the microencapsulated pendimethalin particles is in general from 0.5 to 20% by weight, preferably from 1 to 10% by weight and especially preferred from 2 to 8% by weight, based on the total weight of the microencapsulated pendimethalin particles.

Microencapsulated pendimethalin particles useful for the compositions according to the invention are e.g. known from U.S. Pat. No. 5,705,174 and U.S. Pat. No. 5,910,314, to which full reference is made. Aqueous suspensions of microencapsulated pendimethalin can also be prepared according to processes well-known in the art, e.g. by interfacial condensation as disclosed in U.S. Pat. No. 3,577,515, U.S. Pat. No. 4,280,833 and U.S. Pat. No. 5,310,721.

In a preferred embodiment of the present invention the polymeric wall material is a polyurea. In general, polyureas are formed by reacting a polyisocyanate, having at least two isocyanate groups with a polyamine having at least two primary amino groups to form a polyurea shell wall. Polyisocyanates which are suitable for use include di- and triisocyanates, wherein the isocyanate groups are attached to an aliphatic or cycloaliphatic moiety (aliphatic isocyanates) or to an aromatic moiety (aromatic isocyanates). Examples of suitable aliphatic diisocyanates include tetramethylene diisocyanate, pentamethylene diisocyanate and hexamethylene diisocyanate. Suitable aromatic isocyanates include toluene diisocyanates (TDI: a mixture of the 2,4- and 2,6-isomers), diphenylmethene-4,4'-diisocyanate (MDI: DESMODUR® VL, Bayer Corp., Pittsburgh), polymethylene polyphenyl isocyanate (MONDUR® MR, Bayer Corp., Pittsburgh), PAPI® and PAPI® 135 (Upjohn Co.), 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4"-triphenylmethane triisocyanate. A further suitable diisocyanate is isophorone diisocyanate.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenolisocyanate.

Di- and triisocyanates, such as those mentioned above can be employed individually or as mixtures of two or more such isocyanates.

Suitable polyamines within the scope of this invention will be understood as meaning in general those compounds that contain two and more amino groups in the molecule, which amino groups may be linked to aliphatic or aromatic moieties. Examples of suitable aliphatic polyamines are α,ω-diamines of the formula $$H_2N-(CH_2)_n-NH_2$$

wherein n is an integer from 2 to 6. Exemplary of such diamines are ethylenediamine, propylene-1,3-diamine, tetramethylenediamine, pentamethylenediamine and hexamethylenediamine. A preferred diamine is hexamethylenediamine.

Further suitable aliphatic polyamines are polyethyleneimines of the formula $$H_2N-(CH_2-CH_2-NH)_n-H$$

wherein n is an integer from 2 to 5. Representative examples of such polyethyleneimines are diethylenetriamine, triethylenetetramine, tetraethylenepentamine and pentaethylenehexamine.

Further suitable aliphatic polyamines are dioxaalkane-α,ω-diamines, such as 4,9-dioxadodecane-1,12-diamine of the formula $$H_2N-(CH_2)_3O-(CH_2)_4O-(CH_2)_3-NH_2.$$

Examples of suitable aromatic polyamines are 1,3-phenylenediamine, 2,4- and 2,6-toluenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those polyamines which are insoluble or insufficiently soluble in water may be used as their hydrochloride salts.

Yet further suitable polyamines are those that contain sulfo or carboxyl groups in addition to the amino groups. Examples of such polyamines are 1,4-phenylenediaminoesulfonic acid, 4,4'-diaminodiphenyl-2-sulfonic acid, or diaminomonocarboxylic acids, such as ornithine and lysine.

Polyamines, such as those mentioned above may be used individually or as mixtures of two or more polyamines.

The relative amounts of each complementary wall-forming component will vary with their equivalent weights. In general, approximately stoichiometric amounts are preferred, while an excess of one component may also be employed, especially an excess of polyisocyanate. The total amount of wall-forming components approximately corresponds to the total amount of polymeric wall-forming materials.

The composition according to the invention further contains at least one surface-active substance. Surface-active substances comprise emulsifiers, protective colloids, wetting agents and dispersants that are normally employed in agricultural suspension concentrates and aqueous microcapsule formulations of pesticides. The surface-active substances may be nonionic, anionic and/or cationic. As a rule, the compositions of the present invention contain at least one anionic surfactant, preferably in combination with at least one nonionic surfactant Suitable surfactants which may be used in the compositions of the invention are disclosed e.g. in "McCutcheon's Detergents and Emulsifiers Annual", MC Publishing Corp., Ridgewood, N.J., USA 1981; H. Stache, "Tensid-Taschenbuch", 2$^{nd}$ ed., C. Hanser, Munich, Vienna, 1981; M. and J. Ash, "Encyclopedia of Surfactants", vol. I-III, Chemical Publishing Co., New York, N.Y., USA 1980-1981.

In a preferred embodiment of the invention, the composition contains at least one oligomeric or polymeric surface-active compound A which contains the plurality of anionic groups, such as carboxylate groups, sulfonate groups, phosphonate groups, sulfate groups and/or phosphate groups. The anionic groups in these oligomeric or polymeric compounds may be partially or fully neutralized. Suitable counter ions are sodium, potassium, magnesium, calcium and ammonium. Examples for oligomeric and polymeric substances A are the salts of ethoxylated lignosulfonic acid, of lignosulfonic acid, of oxidized lignins, the salts of styrene-maleic anhydride copolymers, the salts of homo-, co- and terpolymers of acrylic acid, the salts of arylsulfonic acid formaldehyde condensates and of arylsulfonic acid formaldehyde-urea condensates, such as naphthalene sulfonic acid formaldehyde condensates, phenol sulfonic acid formaldehyde condensates, cresol sulfonic acid formaldehyde condensates etc. Preferably, the composition of the invention contains at least one surfactant A which is selected from lignosulfonic acid salts, oxidized alkali lignins and ethoxylated lignosulfonic acid salts. Preferably, the composition of the invention contains the polymeric or oligomeric substance A in amounts of from 1 to 20% by weight, preferably from 2 to 15% by weight and in particular from 4 to 10% by weight, based on the total amount of pendimethalin in the composition. The concentration of the surface-active substance A in the composition is preferably from 5 to 100 g/l in particular from 10 to 80 g/l and most preferred from 20 to 50 g/l.

Preferably, the composition of the invention contains an anionic surface-active compound of formula I $$R-(O-A)_m-O-X$$

wherein
R is a hydrocarbon radical having from 8 to 40 carbon atoms and preferably from 12 to 30 carbon atoms and optionally one oxygen atom;
A is independently from one another 1,2-ethylene, 1,2-propylene or 1,3-propylene, especially 1,2-ethylene;
m is from 3 to 200, preferably from 5 to 100 and especially preferred from 5 to 50; and
X is SO$_3$M or PO$_3$M$_2$ with m being selected from H, alkaline metals, such as K and A, alkaline earth metals, such as Ca and Mg and ammonium. Preferably, M is an alkaline metal and especially sodium.

Examples of suitable hydrocarbon radicals R having from 8 to 40 carbon atoms are alkyl having from 8 to 40 and preferably from 12 to 30 carbon atoms, phenyl, which may be substituted with one or two alkyl radicals having from 4 to 20 carbon atoms, phenyl, which is substituted with a phenoxy radical, wherein phenyl and/or phenoxy may contain an alkyl radical having from 4 to 20 carbon atoms, tristyrylphenyl radical etc.

In a preferred embodiment of the present invention the radical R in formula I is a tristyrylphenyl radical.

In a preferred embodiment of the invention the composition contains both an anionic surface-active substance A and an anionic surface-active compound of the formula I as defined above.

The amount of surface-active compound I is preferably from 1 to 50% by weight, especially from 5 to 30% by weight and most preferred from 8 to 20% by weight, based on the pendimethalin in the composition. In preferred compositions, the concentration of the at least one anionic surface-active compound of formula I is from 5 to 200 g/l, especially from 25 to 150 g/l and most preferred from 40 to 100 g/l.

The compositions according to the invention may also contain a nonionic surface-active compound. Preferred nonionic surface-active compounds are the neutral surface-active compounds of the formula II,

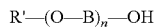

wherein
R' is a hydrocarbon radical having from 8 to 40 and more preferably from 12 to 30 carbon atoms and optionally one oxygen atom,
B is 1,2-ethylene, 1,2-propylene or 1,3-propylene and more preferred 1,2-ethylene, and
n is from 5 to 200, preferably from 8 to 100 and more preferred from 10 to 50.

Examples of suitable hydrocarbon radials R' include the radicals mentioned for R. In a preferred embodiment of the invention the radical R' is a phenyl radical being substituted with one $C_4$-$C_{18}$-alkyl group.

The amount of neutral surface-active compound II is preferably from 1 to 20% by weight, in particular from 2 to 10% by weight and most preferred from 3 to 8% by weight, based on the amount of pendimethalin in the composition. The concentration of the surface-active compound II is preferably from 5 to 100 g/l, in particular from 10 to 50 g/l and most preferred from 15 to 40 g/l.

Apart from the non-encapsulated pendimethalin, the microencapsulated pendimethalin and the surface-active substance composition of the invention may also contain a water-soluble, inorganic salt which results from the preparation of the microencapsulated pendimethalin. Such inorganic salts include alkali metal salts, such as lithium chloride, sodium chloride, potassium chloride, lithium nitrate, sodium nitrate, potassium nitrate, lithium sulfate, sodium sulfate, potassium sulfate, sodium monohydrogen phosphate, potassium monohydrogen phosphate, sodium dihydrogen phosphate, potassium dihydrogen phosphate and the like; alkaline earth metal salts, such as magnesium chloride, calcium chloride, magnesium nitrate, calcium nitrate, magnesium sulfate and the like and ammonium salts, such as ammonium chloride, ammonium sulfate, ammonium monohydrogen phosphate, ammonium dihydrogen phosphate and the like. Preferred salts are sodium chloride, potassium chloride, calcium chloride and magnesium sulfate with magnesium sulfate being especially preferred. The concentration of the water-soluble, inorganic salt may vary from 10 to 200 g/l, preferably from 20 to 180 g/l and especially from 50 to 150 g/l.

In a preferred embodiment of the invention the composition contains
i. 50 to 500 g/l, preferably 100 to 300 g/l and especially 150 to 250 g/l of pendimethalin as microencapsulated pendimethalin particles a),
ii. 50 to 500 g/l, preferably 100 to 300 g/l and especially 150 to 250 g/l of non-encapsulated pendimethalin particles b),
iii. 5 to 100 g/l, preferably 10 to 80 g/l, in particular from 20 to 50 g/l of at least one anionic oligomeric, or polymeric surface-active substance A as defined above,
iv. 5 to 200 g/l, preferably 25 to 150 g/l, especially from 40 to 100 g/l of at least one anionic surface-active compound of the formula I as defined above,
v. 5 to 100 g/l, preferably from 10 to 50 g/l, in particular from 15 to 40 g/l of at least one nonionic surface-active compound of the formula II as defined above, and
vi. 20 to 200 g/l, preferably from 50 to 150 g/l of at least one water-soluble inorganic salt, the total amount of pendimethalin in these compositions being preferably from 200 to 600 g/l and most preferred from 300 to 500 g/l.

The composition of the invention may further contain customary auxiliaries, such as defoamers, thickeners, anti-freezes, preservatives, anti-settling agents etc. which are usually employed in aqueous formulations of pesticides.

Suitable thickening agents include inorganic thickening agents, such as clays, hydrated magnesium silicates and organic thickening agents, such as polysaccharide gums, like xanthan gum, guar gum, gum arabic and cellulose derivatives. Organic thickening agents are employed in amounts of from 0.5 to 30 g/l and preferably from 1 to 10 g/l while inorganic thickening agents are employed in amounts of from 0.5 to 30 g/l and preferably from 1 to 10 g/l.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. In general, the amount of preservatives will be from 0.1 to 10 g/l.

Suitable anti-freezing agents include organic solvents which are completely miscible with water, such as ethylene glycol, propylene glycol, other glycols, glycerin or urea.

Suitable defoamers include polysiloxanes, such as polydimethyl siloxane. Defoamers are usually employed in amounts of from 0.1 to 5 g/l.

The particle size of both the microencapsulated pendimethalin particles and the non-encapsulated pendimethalin particles will in general not exceed 40 μm and preferably 30 μm. Most preferred, both the microencapsulated pendimethalin particles and the non-encapsulated pendimethalin particles have particle sizes (diameters) ranging from 0.5 to 20 μm. The particle sizes given refer to those particle sizes that have 90% by weight of the pendimethalin particles. Preferably the weight-average particle size (diameter) of both the encapsulated and the non-encapsulated pendimethalin particles will range from 1 to 20 μm and especially from 1 to 10 μm. The particle size of the pendimethalin particles can be determined by conventional methods such as light-scattering.

The compositions of the invention can be easily obtained by mixing the first flowable, aqueous composition containing particles of microencapsulated pendimethalin with a second flowable, aqueous composition containing non-encapsulated particles of pendimethalin. In order to achieve the desired concentration of pendimethalin in the composition of the invention, the concentration of pendimethalin particles in said first and said second aqueous composition will vary from 200 to 600 g/l and especially from 300 to 500 g/l.

The mixing of the first and the second composition can be achieved by conventional means for mixing aqueous suspensions (see. The temperature at which mixing is performed is not critical and may in general vary from 0 to 60° C., especially from 10 to 50° C. or 20 to 35° C.

Both the first flowable aqueous composition containing particles of microencapsulated pendimethalin and the second flowable, aqueous composition containing non-encapsulated particles of pendimethalin usually contain at least one surface active ingredient.

In a preferred embodiment the first composition contains at least one surface-active polymeric compound A as defined above. The amount of the surface active compound A in the first composition will usually be from 2 to 40% by weight, preferably from 5 to 30% by weight and especially from 10 to 25% by weight, based on the amount of pendimethalin in the composition. The first composition may further contain customary auxiliaries, such as defoamers, thickeners, anti-freezes, preservatives, anti-settling agents etc. which are usually employed in aqueous formulations of pesticides.

Suitable aqueous compositions containing microencapsulated pendimethalin are known in the art, especially from U.S. Pat. No. 4,874,425, U.S. Pat. No. 5,705,174 and U.S. Pat. No. 5,910,314. Aqueous compositions of microencapsulated pendimethalin particles can be also obtained according to the processes disclosed in U.S. Pat. No. 4,280,833, U.S. Pat. No. 4,640,709, U.S. Pat. No. 4,938,797 and U.S. Pat. No. 5,310,721. Aqueous compositions of microencapsulated pendimethalin are commercially available from BASF Corporation, NC, USA.

In a preferred embodiment the second composition contains at least one surface-active compound of the formula I as defined above. The amount of the surface-active compound I in the second composition will usually be from 1 to 50% by weight, preferably from 10 to 45% by weight and especially from 20 to 40% by weight, based on the amount of pendimethalin in the composition. It is most preferred that the second composition also contains a neutral surface active compound of the formula II as defined above. The amount of the surface-active compound II in the second composition will usually be from 2 to 30% by weight, preferably from 5 to 25% by weight and especially from 7 to 20% by weight, based on the amount of pendimethalin in the second composition. The second composition may further contain customary auxiliaries, such as defoamers, thickeners, anti-freezes, preservatives, anti-settling agents etc. which are usually employed in aqueous formulations of pesticides.

Suitable suspension concentrates containing non-encapsulated pendimethalin particles are also known from the art, e.g. from EP 249 770, EP-A-249 075, EP 404 201, U.S. Pat. No. 4,874,425 and EP-A-445 603. Suspension concentrates of pendimethalin are also commercially available from BASF Corporation, N.C., USA.

The compositions according to the invention are useful for controlling undesirable plants. Due to their higher storage stability, especially at temperature exceeding 30° C., especially at 35° C. or higher and even at temperatures exceeding 45° C. the compositions are easy to handle. Advantageously the compositions of the invention do not suffer from a slowed release of the active ingredient Consequently the compositions are easier to handle than conventional concentrate compositions of pendimethalin. Thus, the present application also relates to the use of the compositions for controlling undesired vegetation.

The compositions according to the present invention can be easily diluted with water to the desired application concentration which is familiar. Thus obtained diluted compositions are ready to use and therefore usually referred to application form or as a tank-mix. The tank-mix obtained by diluting the compositions of the invention with can be applied before (preemergence), during and/or after the emergence of undesired plants (postemergence). Therefore the invention also relates to a method for controlling undesired vegetation, which comprises applying an aqueous tank-mix, which is obtained by diluting a composition according to the invention with water, before, during and/or after the emergence of undesired plants.

The amount of water being used to dilute the concentrate composition of the invention will usually be from 10 to 10000 times the volume of the concentrate composition.

The tank-mix can be also be applied together with the seed of a crop plant. There is also the possibility of applying the compositions of the invention by applying seed of a crop plant pretreated with a diluted application form of the compositions of the invention. Preferably the compositions according to the invention are applied to the leaves of the undesired plants. Especially the diluted composition is applied in a manner such that the leaves of the crop plants are, wherever possible, not sprayed, while the composition reaches the leaves of the undesired (target) plants growing below or the exposed soil surface (post-directed or lay-by application). The application rates which are necessary to achieve the desired control are similar to those application rates required when using a conventional suspension concentrate of pendimethalin.

The examples below illustrate the present invention:

A first aqueous composition (1) containing about 450 g/l of pendimethalin as microencapsulated pendimethalin particles of a diameter below 20 μm are blended with equal amounts of a commercially suspension concentrate (2) containing about 400 g/l of non-encapsulated pendimethalin particles having a diameter below 20 μm.

The composition (1) of the microencapsulated pendimethalin particles is obtained according to the general method disclosed in example 1 of U.S. Pat. No. 5,705,174 using the following ingredients:

450.0 g/l of pendimethalin 77.6 g/l of the sodium salt of an oxidized alkali lignin [1]
   1) Diwatex® 200 of Lignotech, Rothschild, Wis., USA 6.0 g/l of the sodium salt of a naphthaline sulfonic acid formaldehyde condensate [2]
   2) Morwet D 425, Witco, Greenwich, Conn., USA 212.0 g/l of magnesium sulfate heptahydrate 15.3 g/l of an aromatic diisocyanate [3]
   3) Mondur® MRS, supplied by Bayer, Pittsburgh, Pa., USA 9.0 g/l of a 60% aqueous solution of 1,6-hexane diamine and water ad 1.0 l. The thus obtained aqueous suspension of microencapsulated pendimethalin particles was further blended with preservatives, antifoam and thickener.

The suspension concentrate of pendimethalin (2) had the following composition:

400.0 g/l of pendimethalin 125.0 g/l of the potassium salt of an ethoxylated polyarylphenol phosphate [4]
   4) Soprofor® FLK, Rhodia, Milano, Italy 50.0 g/l of a nonylphenol ethoxylate [5]
   5) Arkopal® N 080, Clariant, Frankfurt, A.M. Germany and conventional auxiliaries (an organic thickener, an inorganic thickener, an antifoam and an anti-selling agent) in a total concentration of about 21 g/l and water ad 1.0 l.

Storage Stability:

In order to evaluate the storage stabilities the composition of the invention as well as the suspension concentrate and the suspension of microencapsulated pendimethalin were stored for 12 weeks at 45° C. and also for 26 weeks at 37° C. An assessment of storage stability is made by the quantity of material retained on 1-50 μm and on 45 μm sieves following dilution of the product in water. The initial value and the values after 12 weeks and 26 weeks are given in table 1. Moreover, the suspension concentrate of pendimethalin as well as the blend according to the invention had been stored at 37° C. for 12 weeks or 26 weeks respectively and the storage stability was assessed as outlined above. The values are given in table 1.

TABLE 1

| Storage period | Composition of the invention retention [%] [1] | | Suspension concentrate retention [%] [1] | | Microcapsule composition retention [%] [1] | |
|---|---|---|---|---|---|---|
| | 150 μm | 45 μm | 150 μm | 45 μm | 150 μm | 45 μm |
| initial | 0 | <0.01 | | | | |
| 12 weeks 45° C. | <0.01 | 0.03 | 0.51 | 0.74 | <0.01 | 0.02 |
| 12 weeks 37° C. | n.d. | n.d. | 0.024 | 0.05 | n.d | n.d. |
| 26 weeks 37° C. | <0.01 | <0.02 | 0.01 | 0.06 | 0.006 | 0.023 |

[1] % by weight, based on the amount of pendimethalin in the composition

As can be seen from the data in table 1, the storage stability of the composition of the invention is comparable to the storage stability of conventional microencapsulated pendimethalin and better than the storage stability of conventional suspension concentrate.

The invention claimed is:

1. A flowable, aqueous concentrate composition containing
   i. 50 to 500 g/l of pendimethalin as microencapsulated pendimethalin particles a) and wherein the microencapsulated pendimethalin is encapsulated by a polymeric wall material which is selected from the group consisting of polyurea and polyurethane, and wherein the polymeric wall material is water insoluble,
   ii. 50 to 500 g/l of non-encapsulated pendimethalin particles b),
   iii. 5 to 100 g/l of at least one anionic oligomeric or polymeric surface-active substance A which is an anionic oligomer or polymer, which contains a plurality of anionic groups,
   iv. 5 to 200 g/l of at least one anionic surface-active compound of the formula I R—(O-A)$_m$-O—X wherein
   R is a hydrocarbon radical having from 8 to 40 carbon atoms and optionally one oxygen atom,
   A is 1,2-ethylene, 1,2-propylene or 1,3-propylene,
   m is from 3 to 200 and
   X is $SO_3M$ or $PO_3M_2$ with M being selected from the group consisting of H, alkaline metal, alkaline earth metal and ammonium,
   v. 5 to 50 g/l of at least one nonionic surface-active compound of the formula II $R^1$—(O—B)$_n$—OH wherein
   $R^1$ is a hydrocarbon radical having from 8 to 40 carbon atoms and optionally one oxygen atom,
   B is 1,2-ethylene, 1-2-propylene or 1,3-propylene and
   n is from 5 to 200,
   vi. 10 to 200 g/l of at least one water-soluble inorganic salt, and
   wherein the weight ratio of the microencapsulated pendimethalin particles to non-encapsulated pendimethalin particles is from 1:9 to 9:1.

2. The composition as claimed in claim 1, wherein the microencapsulated pendimethalin particles are encapsulated by a polymeric wall material in an amount of from 0.5 to 20% by weight, based on the weight of pendimethalin in said particles.

3. The composition as claimed in claim 1, wherein the concentration of pendimethalin in the composition is from 200 to 600 g/l.

4. The composition as claimed in claim 1, wherein the composition contains at least one surface-active substance A which contains a plurality of anionic groups and which is an anionic oligomer or polymer.

5. The composition as claimed in claim 4, wherein the anionic oligomer or polymer is selected from the group consisting of oxidized alkali-lignin, lignosulfonate, ligninsulfate, and a salt of an arylsulfonic acid formaldehyde condensate and of an arylsulfonic acid formaldehyde urea condensate.

6. The composition as claimed in claim 1, wherein the composition contains at least one neutral surface-active compound of formula II $R^1$—(O—B)$_n$—OH wherein
   $R^1$ is a hydrocarbon radical having from 8 to 40 carbon atoms and optionally one oxygen atom,
   B is 1,2-ethylene, 1-2-propylene or 1,3-propylene and
   n is from 5 to 200.

7. The composition as claimed in claim 1, wherein the total amount of surface-active substance is from 1 to 50% by weight, based on the weight of pendimethalin in the composition.

8. A method for preparing a composition as claimed in claim 1, which comprises mixing of a first free flowable, aqueous composition containing particles of microencapsulated pendimethalin containing of from 200 to 600 g/l of pendimethalin with a second free flowable aqueous composition containing 200 to 600 g/l of non-encapsulated particles of pendimethalin.

9. A method for controlling undesired vegetation, which comprises applying an aqueous tank-mix, which is obtained by diluting a concentrate composition as claimed in claim 1 with water, to undesired plants, their seed or their environment before, during and/or after the emergence of the undesired plants.

10. The composition of claim 1, wherein the polymeric wall material is a polyurea which is obtained by reacting a di- or polyisocyanate with a di- or polyamine.

11. A method for controlling undesired vegetation comprising applying to the unwanted vegetation, their seed or their environment a herbicidally effective amount of an aqueous composition containing
   i. 50 to 500 g/l of pendimethalin as microencapsulated pendimethalin particles a) and wherein the microencapsulated pendimethalin is encapsulated by a polymeric wall material which is selected from the group consisting of polyurea and polyurethane, and wherein the polymeric wall material is water insoluble, ii. 50 to 500 g/l of non-encapsulated pendimethalin particles b), iii. 5 to 100 g/l of at least one anionic oligomeric or polymeric surface-active substance A which is an anionic oligomer or polymer, which contains a plurality of anionic groups, iv. 5 to 200 g/l of at least one anionic surface-active compound of the formula I

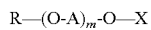

wherein

R is a hydrocarbon radical having from 8 to 40 carbon atoms and optionally one oxygen atom, A is 1,2-ethylene, 1,2-propylene or 1,3-propylene, m is from 3 to 200 and X is $SO_3M$ or $PO_3M_2$ with M being selected from the group consisting of H, alkaline metal, alkaline earth metal and ammonium, v. 5 to 50 g/l of at least one nonionic surface-active compound of the formula II

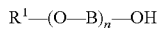

wherein $R^1$ is a hydrocarbon radical having from 8 to 40 carbon atoms and optionally one oxygen atom, B is 1,2-ethylene, 1-2-propylene or 1,3-propylene and n is from 5 to 200, vi. 10 to 200 g/l of at least one water-soluble inorganic salt, and wherein the weight ratio of the microencapsulated pendimethalin particles to non-encapsulated pendimethalin particles is from 1:9 to 9:1.

12. The method of claim 11, wherein the aqueous composition is applied to leaves of undesired vegetation.

13. The method of claim 11, wherein the polymeric wall material is a polyurea which is obtained by reacting a di- or polyisocyanate with a di- or polyamine.

* * * * *